United States Patent [19]

Faraj et al.

[11] Patent Number: 5,420,357
[45] Date of Patent: May 30, 1995

[54] PREPARATION OF DIALKYL PEROXIDES

[75] Inventors: Mahmoud K. Faraj, Newtown Square; Frank J. Liotta, Jr., Collegeville; Haven S. Kesling, Jr., Drexel Hill, all of Pa.

[73] Assignee: Arco Chemical Technology, L.P., Greenville, Del.

[21] Appl. No.: 102,017

[22] Filed: Aug. 4, 1993

[51] Int. Cl.⁶ .......................................... C07C 409/00
[52] U.S. Cl. .................................. 568/578; 568/558
[58] Field of Search ............................. 568/558, 578

[56] References Cited

U.S. PATENT DOCUMENTS 2,403,758  7/1946  Rust et al. .
2,403,771  7/1946  Vaughan et al. .
2,630,456  3/1953  Bell et al. .
2,862,973  12/1958  Winkler .
3,626,014  12/1971  Harvey .
4,198,528  4/1980  Kelsey .
4,374,280  2/1983  Messina et al. .

FOREIGN PATENT DOCUMENTS 839312  4/1970  Canada .

OTHER PUBLICATIONS

Imelik et al Catalysis by Zeolites (1980) pp. 343–350.
"Organic Peroxides. Part III. The Preparation of Alkyl Hydroperoxides and Dialkyl Peroxides. Characteristic Derivatives of Alkyl Hydroperoxides." Davies, et al., J. Chem. Soc., pp. 2200–2204 (1954).

*Primary Examiner*—Alan Siegel
*Attorney, Agent, or Firm*—William C. Long

[57] ABSTRACT

The present invention provides a process for the production of dialkyl peroxides by reaction of an alcohol and/or an olefin with an organic hydroperoxide, using a solid acidic zeolite catalyst.

4 Claims, No Drawings

PREPARATION OF DIALKYL PEROXIDES

BACKGROUND OF THE INVENTION

1. Field of the Invention

The present invention relates to the production of dialkyl peroxides such as ditertiary butyl peroxide by the reaction of an alcohol such as tertiary butyl alcohol and/or an olefin such as isobutylene with a hydroperoxide such as tertiary butyl hydroperoxide in the presence of a solid acidic zeolite catalyst.

2. Description of the Prior Art

The preparation of dialkyl peroxides by the reaction of an alcohol such as tertiary butyl alcohol (TBA) with an organic hydroperoxide such as tertiary butyl hydroperoxide (TBHP) is known. See, for example, U.S. Pat. Nos. 2,403,771, 2,403,758, 2,862,973, 3,626,014 and the like. The preparation of dialkyl peroxides by the reaction of an olefin such as 2-methylbut-2-ene with an organic hydroperoxide such as TBHP is also known. See Davies, et al., J. Chem. Sec. page 2200, 1954.

In such prior processes, catalysts such as sulfuric acid, sulfonic acid resins having a low degree of cross-linking and the like have been employed. The use of such catalysts has a number of disadvantages including the corrosion and safety hazards associated with the use of sulfuric acid, catalyst deactivation and deterioration associated with the use of catalyst resins and the like. Canadian Patent 839,312, for example, shows the production of ditertiary butyl peroxide by the reaction of TBA with TBHP using a gel-type 4% cross-linked sulfonic acid resin with the requirement that water be azeotropically removed as with chloroform in order for the reaction to proceed.

The preparation of organic hydroperoxides by reaction of an alcohol such as TBA with hydrogen peroxide using an inorganic heteropoly acid is shown in U.S. Pat. No. 2,630,456.

BRIEF DESCRIPTION OF THE INVENTION

In accordance with the present invention, a process is provided for the production of dialkyl peroxides wherein an alcohol and/or an olefin is reacted with an organic hydroperoxide in the presence of a solid natural or synthetic acidic aluminosilicate zeolite catalyst. The catalysts employed are at least partially acidic, i.e., not all acidic sites are neutralized; the catalysts are oxidatively resistant and demonstrate high activity for the desired reaction over extended times. The use of the solid catalyst is advantageous in that the reaction mixture is readily separated from the catalyst by conventional procedures.

DETAILED DESCRIPTION

The process of the present invention can be represented by the following equations:

$$ROH + R_1OOH \longrightarrow ROOR_1 + H_2O \quad (1)$$

or

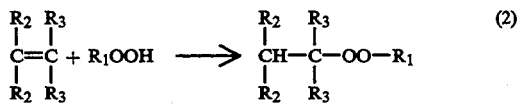

$$\underset{\underset{R_2}{|}}{\overset{\overset{R_2}{|}}{C}}=\underset{\underset{R_3}{|}}{\overset{\overset{R_3}{|}}{C}} + R_1OOH \longrightarrow \underset{\underset{R_2}{|}}{\overset{\overset{R_2}{|}}{CH}}-\underset{\underset{R_3}{|}}{\overset{\overset{R_3}{|}}{C}}-OO-R_1 \quad (2)$$

wherein R and $R_1$ are the same or different alkyl groups having 1 to 10 carbon atoms, $R_2$ and $R_3$ are hydrogen or R. Preferably, R and $R_1$ are the same tertiary alkyl group having 4 or 5 carbon atoms, i.e. tertiary butyl or tertiary amyl groups, $R_2$ is R and $R_3$ is hydrogen.

In especially preferred practice of the invention, ditertiary butyl peroxide is prepared by the reaction of tertiary butyl hydroperoxide with tertiary butyl alcohol and/or isobutylene, and ditertiary amyl hydroperoxide is prepared by the reaction of tertiary amyl hydroperoxide with tertiary amylene. Dialkyl peroxides where the alkyl groups are different, such as tertiary butyl tertiary amyl peroxide, can be prepared for example by reacting tertiary amyl alcohol and/or tertiary amylene with tertiary butyl hydroperoxide.

In carrying out the process of the present invention, it is generally desirable to provide at least 0.5 mols of alcohol and/or olefin per mol of hydroperoxide to the reaction. Preferably, at least 1 mol of alcohol and/or olefin per mol of hydroperoxide is employed up to about 5 mols of alcohol and/or olefin per mol of hydroperoxide. The use of alcohol and/or olefin in at least equimolar amounts relative to the hydroperoxide provides good reaction rates and high conversions of the reactants.

The reaction of the invention can be carried out using either alcohol or olefin to react with the hydroperoxide. Preferably, however, mixtures of 0.1 to 10 mols of alcohol per mol of olefin are employed.

The process of the invention is carried out at temperatures sufficiently high to ensure a satisfactory reaction rate but not so high as to cause substantial decomposition of the hydroperoxide. Generally, temperatures ranging from about 20° C. to 150° C. and preferably 40° C. to about 110° C. are employed. The reaction takes place in the liquid phase, and the system pressure is maintained at a level sufficient to ensure the liquid phase reaction. Pressures in the range 0.2 to 100 atmospheres gauge are illustrative.

Essential to practice of the invention is the use of an inorganic oxidatively resistant zeolitic solid acid catalyst in the hydrogen form. As a result of the use of such catalysts, water removal requirements, previously required, are not necessary in carrying out the process.

Generally, any of the natural or synthetic aluminosilicate zeolites which are at least partially in the acid form can be used. Partially exchanged Y-zeolite of the general formula $M_xH_{1-x}$ Y-zeolite can be used where x is the molar fraction of exchangeable cations and where $0 \leq X \leq 0.95$. M is an alkali, alkaline earth and/or transition metal. Ultra stable Y-zeolite, mineral clays and acid washed clays such as Montmorillonite K-10 or KSF are suitable. Acid washed mineral zeolite such as chabazite, ferrierite and the like can be employed. Other specific examples include H ZSM-5, mordenite and the like. It is important that at least 5% and preferably at least 50% of the acidic sites of the catalyst which is employed not be neutralized.

In practice of the invention sufficient of the zeolite catalyst is employed to ensure a satisfactory conversion and selectivity. It is generally advantageous to contact the reactants with a bed of the solid catalyst, although other techniques such as slurry contact can be used. Continuous procedures are preferred, although batch techniques can be used.

In an especially preferred embodiment of the invention, isobutane oxidate which is produced in accordance with known oxidation procedures and which is comprised mainly of TBA and TBHP, after removal of unreacted isobutane, is directly reacted to form ditertiary butyl peroxide in accordance with the invention. U.S. Pat. Nos. 2,845,461, 3,478,108 and 4,408,081 describe the isobutane oxidation.

In order to more clearly illustrate the invention, the following examples are provided.

EXAMPLE 1

A debutanized isobutane oxidate together with added isobutylene is reacted in accordance with the invention to form DTBP. The oxidate contains about 58 wt. % TBA, about 40 wt. % TBHP, with the remainder comprised of methanol, acetone, water and traces of other organic materials. The mol ratio isobutylene/TBHP is 2.5/1 and Hydrogen Y zeolite in amount of 30 wt. % based on oxidate is used. The mixture is heated under nitrogen to 85° C. with stirring in a parr reactor for 3 hours. TBHP conversion is 95+%, and the reaction selectivity to DTBP based on TBHP converted is 92%.

EXAMPLES 2–5

In a similar fashion, isobutane oxidate as described in Example 1 is reacted in the presence of varying amounts of Hydrogen Y zeolite in the parr reactor for 5 hours at 85° C. but without added isobutylene. The results obtained are shown in the following table:

TABLE 1

| Catalyst Wt. % on Oxidate | TBHP Conversion % | Selectivity to DTBP based on TBHP |
|---|---|---|
| 5 | 16 | 89 |
| 10 | 21 | 88 |
| 20 | 28 | 92 |
| 38.5 | 63 | 91 |

From the results described above, it can be seen that the present invention provides a highly efficient method for the preparation of dialkyl peroxides.

I claim:

1. A process for the preparation of a dialkyl peroxide having the formula $ROOR_1$ which comprises reacting a reagent selected from the group consisting of an alcohol having the formula ROH, and olefin having the formula:

and mixtures in the liquid phase with a hydroperoxide having the formula $R_1OOH$, at a temperature of 20°–150° C. and at a pressure sufficient to maintain the liquid phase in the presence of an effective amount of a solid acidic aluminosilicate zeolite catalyst, in the above formulae R and $R_1$ are alkyl groups having 1 to 10 carbon atoms, and $R_2$ and $R_3$ are hydrogen or R.

2. The process of claim 1 wherein the said catalyst is Hydrogen Y zeolite.

3. A process for the preparation of ditertiary butyl peroxide which comprises reacting tertiary butyl alcohol and/or isobutylene with tertiary butyl hydroperoxide in the presence of an effective amount of a solid acidic aluminosilicate zeolite catalyst.

4. A process for the preparation of ditertiary amyl peroxide which comprises reacting tertiary amyl alcohol and/or tertiary amylene with tertiary amyl hydroperoxide in the presence of an effective amount of a solid acidic aluminosilicate zeolite catalyst.

* * * * *